United States Patent
Gilderdale et al.

[11] Patent Number: 5,876,338
[45] Date of Patent: Mar. 2, 1999

[54] NUCLEAR MAGNETIC RESONANCE IMAGING APPARATUS

[75] Inventors: David John Gilderdale, South Devon, United Kingdom; Anthony Charles Grantham, Small Field, United Kingdom

[73] Assignee: Picker International, Inc., Cleveland, Ohio

[21] Appl. No.: 991,499

[22] Filed: Dec. 16, 1997

[51] Int. Cl.⁶ .................................................... A61B 1/00
[52] U.S. Cl. ............................ 600/411; 600/127; 600/117
[58] Field of Search ................................. 600/127, 129, 600/410, 411, 420, 421, 422, 423, 103, 117, 118, 153, 104

[56] References Cited

U.S. PATENT DOCUMENTS 4,960,106 10/1990 Kubokawa et al. .
5,035,231 7/1991 Kubokawa et al. .
5,427,103 6/1995 Koji Fujio et al. .
5,445,151 8/1995 Darrow et al. .

FOREIGN PATENT DOCUMENTS 0 385 367 A 9/1990 European Pat. Off. .

*Primary Examiner*—Beverly M. Flanagan
*Attorney, Agent, or Firm*—Timothy B. Gurin; John J. Fry; Eugene E. Clair

[57] ABSTRACT

An MR compatible endoscope 1 has associated MR saddle coil 10 mounted on a removeable former 9. The tip 2 of the endoscope has the usual service channels for imaging. The coil 10 provides an additional MR signal. To avoid the need to plug the coil 10 in, it is inductively couples to a pick-up coil 13 and, to enable this to be removable as will from the endoscope, this may be located in one of the service channels 7 of the endoscope. The removable nature of the coil permits easy repair and, more importantly, a range of coils to be fitted to the endoscope to accommodate different magnetic field strengths.

20 Claims, 3 Drawing Sheets

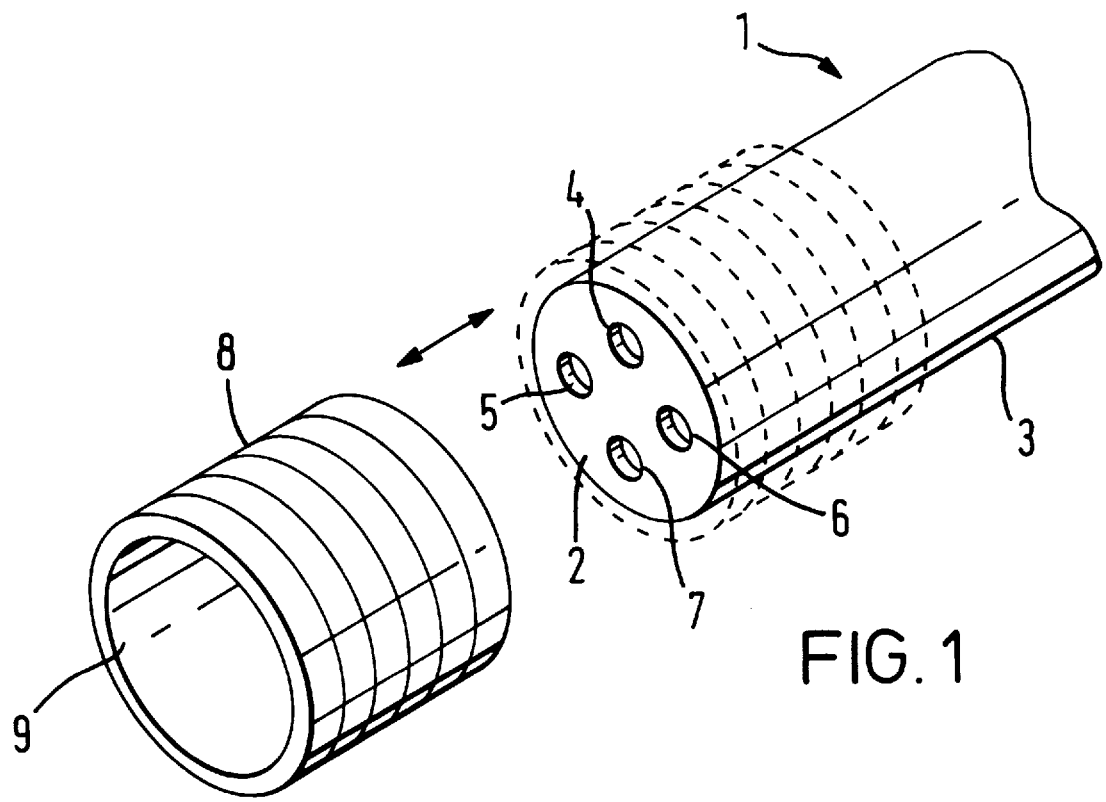
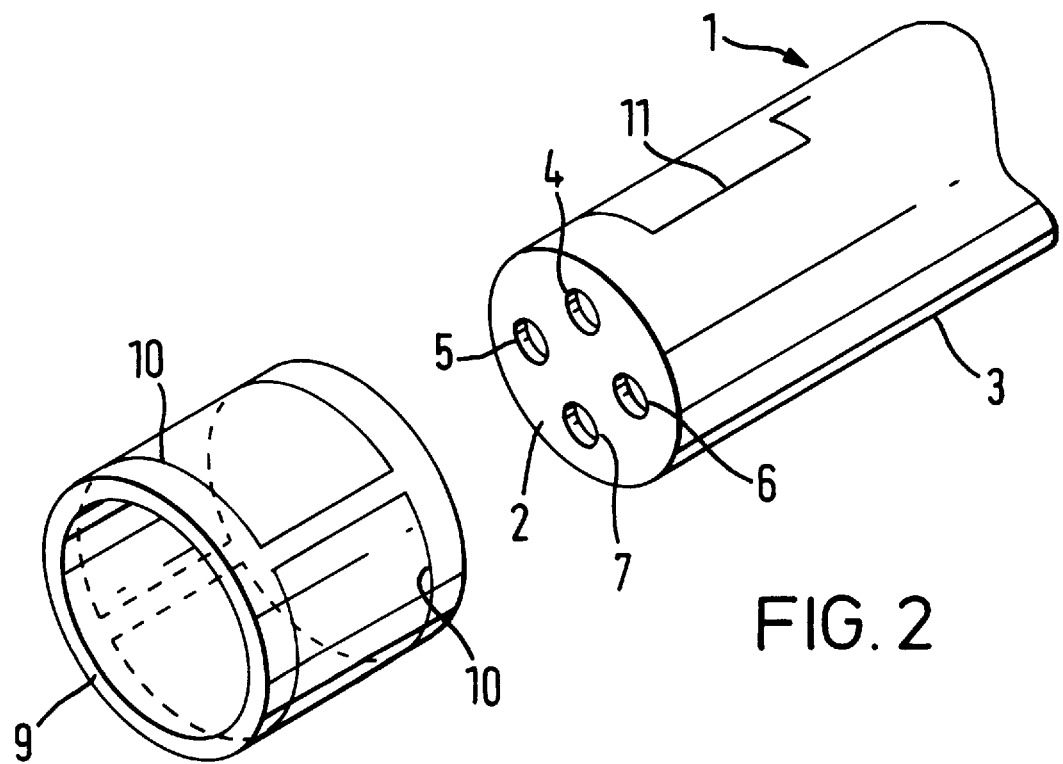

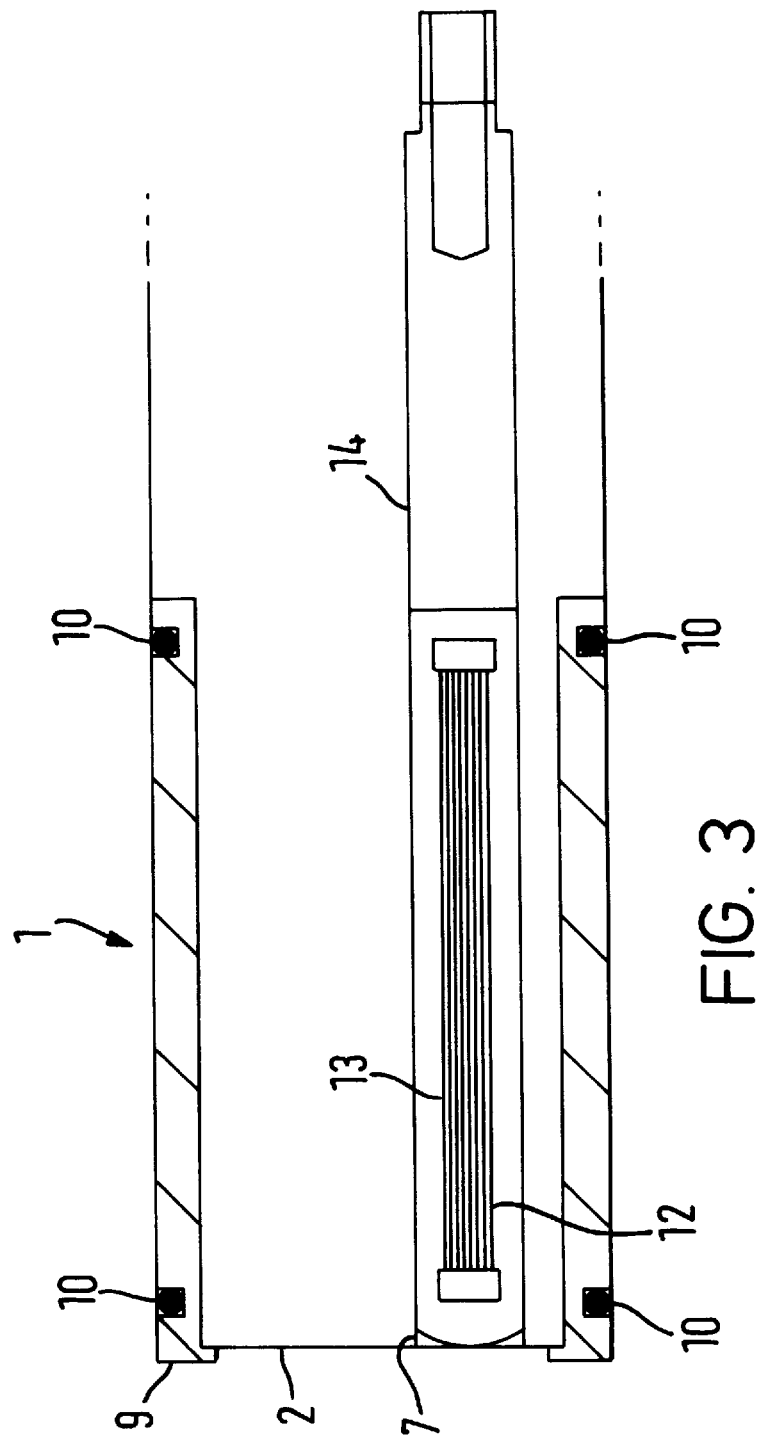

NUCLEAR MAGNETIC RESONANCE IMAGING APPARATUS

TECHNICAL FIELD

The present invention relates to Nuclear Magnetic Resonance Imaging Apparatus (MRI) and more particularly to devices for use with such apparatus.

BACKGROUND OF THE INVENTION

Magnetic resonance imaging (MRI) is used in medicine to produce images of the internal organs of a patient being examined. In MRI, a static magnetic field is applied to the body of the patient to define an equilibrium axis of magnetic alignment in the region of the body being examined. A radio frequency field is then applied to the region being examined in a direction orthogonal to the static magnetic field direction to excite magnetic resonance in the region. This resonance produces signals in r.f. coils placed adjacent the body. Normally separate coils are used for excitation and detection although the same coil or coils may be used for both purposes. The detected signals are processed to produce signals representing an image of the patient's body and this image is visually displayed. In so-called interventional MRI devices such as catheters, biopsy needles and endoscopes may be physically introduced into the body. The term endoscope is intended to encompass colonoscopes, laparoscopes, cystoscopes and gastroscopes.

The present invention is particularly concerned with the provision of endoscopes which are suitable for use with MRI, such endoscopes having a built-in miniature r.f. coil. Examples of such endoscopes are described in U.S. Pat. No. 4 960 106 and U.S. Pat. No. 5 035 231. It has been proposed in the former patent to make such a coil removable to obtain a better optical field of view when required, but this would cause sealing problems.

In addition, there are a wide variety of MRI systems both in terms of construction and the power of the main magnetic field and therefore, because of the variety of main magnetic fields provided by different designs of MRI equipment each such coil must be tailored/tuned to the appropriate main magnetic field strength. Hitherto, it has been necessary for the MRI equipment user to have a range of particular endoscopes each of which has a different coil to suit a particular main magnetic field strength.

SUMMARY OF THE INVENTION

The invention provides an MR compatible endoscope provided with a set of interchangeable miniature r. f. receive coils having different operating characteristics, so that the same endoscope can be used with a variety of MRI systems having different main magnetic field strengths, when in use.

Advantageously, each receive coil of the set is carried by a detachable former which is demountable with respect to the distal end of the endoscope.

The invention also provides an MR compatible endoscope comprising an r.f. receive coil carried by a detachable former which is demountable with respect to the distal end of the endoscope, and a pick-up coil in the distal end of the endoscope, so that in use the receive and pick-up coils are inductively coupled thereby to enable a signal from the receive coil to pass to the proximal end of the endoscope via the pick-up coil.

The principle of inductive coupling could be used even if the endoscope had a single removable receive coil rather than a set of coils. The avoidance of the need for plugs and sockets would be an advantage, and the removable nature of the coil would give advantages from the point of view of replacement or repair of the coil.

How the invention may be carried out will now be described by way of example only and with reference to the accompanying drawings, in which:

BRIEF DESCRIPTION OF THE DRAWINGS

FIG. 1 is a fragmentary perspective view of a first endoscope constructed according to the present invention;

FIG. 2 is a fragmentary perspective view of a second endoscope constructed according to the invention with a different receive coil to that illustrated in FIG. 1;

FIG. 3 is a fragmentary axial cross-section of a third endoscope constructed according to the present invention.

Like reference numerals are given to like parts throughout all the drawings.

DETAILED DESCRIPTION

Figure 4:
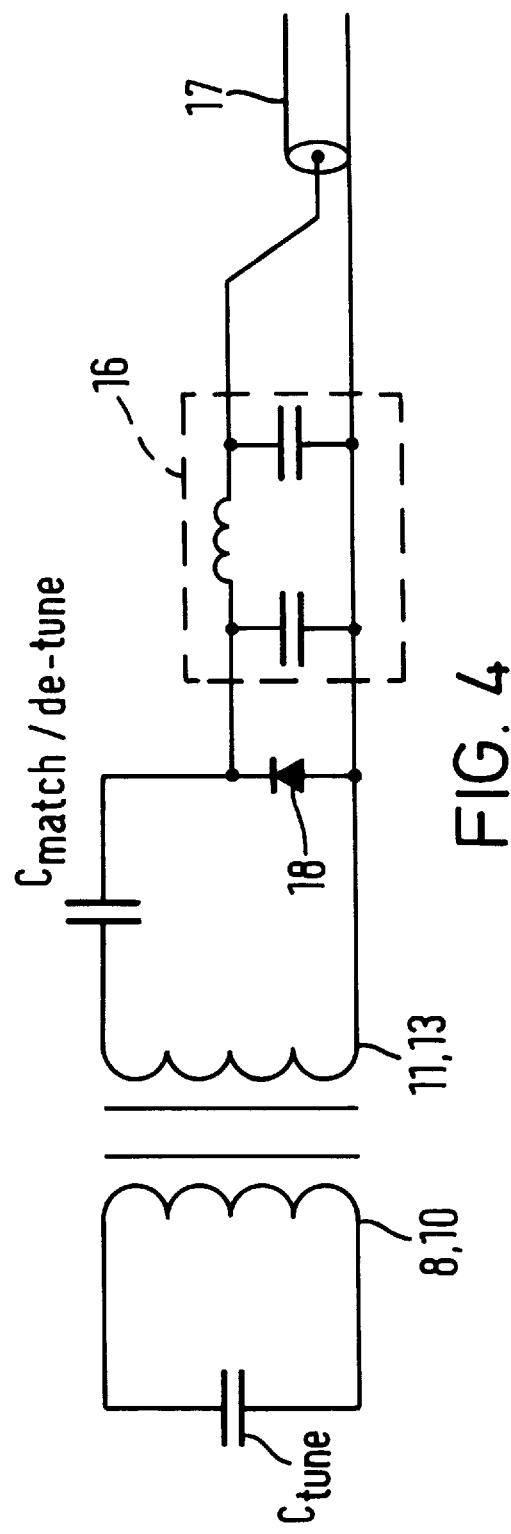
FIG. 4 is a circuit diagram of the receive coil and pick-up coil of FIGS. 1 to 3.

The first endoscope 1 has a distal end 2 which in use is inserted into a patient in order to enable an optically derived image of a target area to be obtained in known manner.

The endoscope body is in the form of an elongate cylindrical member 3 which has a number of internal passages 4, 5, 6 and 7 extending along its length, and is flexible except over the distal end portion.

The passages enable light to be shone down the body 3, to illuminate the target area, and the reflected light to be transmitted back up the body to be converted into an image visible to the operator, in known manner. For example, two passages could each contain an optical fibre bundle, one for illuminating the region in front of the tip of the endoscope, the other for imaging the scene. The other two passages could be for services, for example, suction to remove fluids and for instruments.

The first endoscope 1 is provided with a removable miniature r.f. coil 8 which is carried on a tubular former 9 having a circular cross section and an internal diameter only just greater than the external diameter of the cylindrical body member 3 of the endoscope so that the former 9 can be slid over the rigid end portion of the endoscope and be a snug fit thereon. Attachment means (not shown) prevent it from becoming dislodged during the insertion of the endoscope into the patient or its removal therefrom, as well as ensuring its attachment at the correct angular position.

The removable, or demountable, coil 8 is one of a set each of which has basically the same construction of former 9 but with different performance specifications of coil each designed to operate in a particular strength of main magnetic field and/or with a particular field orientation. The members of the set of coils are thus interchangeable with respect to the single endoscope. A variety of coil configurations could be provided to suit different applications.

The miniature r.f. coil 8 enables the visualisation of the internal structure of a target area to be achieved in addition to the viewing of the external structure by means of the normal optical facility of the endoscope. In other words as well as making the known type of optical examination of the patient by means of the known type of endoscope it is also possible to obtain MRI visualisation of the internal structure of the target area being examined.

In order to achieve the latter the output signal of the coil 8 needs to be coupled to the MR scanner (not shown). To this end, a secondary miniature (pick-up) r.f. coil (not shown) is housed in the distal end of the endoscope and it and the coil 8 are magnetically (inductively) coupled to one another. The secondary (pick-up) coil is connected to the proximal end of the endoscope by a 50 ohm coaxial cable passing along one of the channels 4–7 or buried in and integral with the wall of the body 3.

Instead of inductive coupling, it would be possible to electrically connect the coil 8 to the equipment at the proximal end of the endoscope directly by a miniature 50 ohm coaxial cable which passes though one of the passages or channels 4, 5, 6 or 7 in the body 3 of the endoscope, or which is buried in and integral with the wall of the body 3 of the endoscope.

By providing the endoscope with a detachable r.f. coil (rather than making it integral with the endoscope) there is also the advantage that the cost of modification or repair of the miniature r.f. coil 8 would be lower than if it were integrated with the endoscope itself.

Referring to FIG. 2, the second endoscope differs from the first in that the receive coil consists of a pair of saddle coils 10 and in that one particular form of pick-up coil 11 is illustrated. Thus, the receive coil consists of a pair of rectangular coils 10 which have been wrapped around the curved surface of the former 9. Each coil includes a tuning capacitor (not shown). The former 9 is slid over the distal end of the endoscope 3 in use, and the receive coils 10 inductively couple to the pick-up coil 11. The pick-up coil is contained within the endoscope body 3, and is rectangular, and wrapped around the internal periphery of the cylindrical wall of the endoscope. The pick-up coil also includes a capacitor (not shown) for matching to a coaxial cable to run along the length of the endoscope inside it. The attachment means (not shown) ensures that the former is carried at the correct angular position to ensure that the appropriate coupling between the receive coil and pick-up coil takes place.

The different configuration of the receive coils in FIG. 2 can be more useful in certain circumstances than the cylindrical arrangement in FIG. 1, depending on the body region where the endoscope is inserted. It would be normal for the main exciting field to extend axially along the length of the patient's body in the case of an electro-magnet and vertically through a patient's body in the case of an open magnet. The magnetisation induced in the patient by the r.f. exciting field will be related to the direction of the main field, and the construction of FIG. 2 receives a magnetic resonance signal over a wider range of angles than would the cylindrical coil of FIG. 1.

As with the first embodiment, different saddle coil sizes may be appropriate for different clinical applications, and/or saddle coils may require different capacitance values for tuning to different main field strengths, and a range of saddle coil characteristics is therefore provided on respective formers 9. The appropriate coil is then slid over the end of the endoscope 1, and the magnetic resonance signal is inductively picked up by the coil 11 carried in the body of the endoscope.

Referring to FIG. 3, the third endoscope differs from the second in that the inductive pick-up coil 11 is now mounted in one of the service channels 7. The other service channels are not shown in FIG. 3. The pick-up coil is wound on a long former having a square cross-section at right angles to its length. Clearly the periphery of the former is restricted because it is contained within the narrow service channel 7 and, in order to achieve a 50 ohm match to the main coil, the pick-up coil may be multi-turn. The coil 12 and former 13 are rigidly contained within a probe 14 which in use is inserted along the service channel 7, or along any of the other service channels as desired. The probe is directly connected to a 50 ohm cable, in order to couple the pick-up coil up to receiving electronics (not shown). Both pick-up coil and cable may be removable from the endoscope channel to provide maximum versatility.

Means (not shown) is provided to enable the probe to be accurately located axially within the service channel 7 after it has been inserted.

The receive coil of the embodiment of FIG. 3 is the same saddle coil as for the embodiment of FIG. 2. The conductors are, however, recessed into the surface of the former 9.

The advantages of using the inductively-coupled, tip-mounted coils of FIGS. 1 to 3 are the ability to use a single endoscope at a variety of different field strengths, allowing both MRI (magnetic resonance imaging) and MRS (magnet resonance spectroscopy) studies to be performed, along with the possibility for coil replacement or repair without disturbing the endoscope. The version of FIGS. 1 and 2 required a coupling coil to be built into the endoscope.

The version of FIG. 3 has the further advantage that, since the pick-up coil is mounted in one of the endoscope service channels, all the coils are detachable from the endoscope, which is therefore free from all in-built electronics.

The coil systems of all three versions, as is usual with MRI receive-only coil systems, are desirably tuned and matched so as to allow for low-loss signal transmission via a 50 ohm cable. In addition, it is necessary to minimise current flowing in the receiver coil during the $B_1$ excitation period. With receive coils directly coupled to magnetic resonance processing electronics, this requirement is achieved by introducing a high impedance 'trap' circuit in series with the main coil, controlled electronically by a PIN diode switch. When operative, the trap de-tunes the receive coil, minimising its coupling with the $B_1$ field. It would not be possible to control a PIN diode in the receive coils in this indirectly coupled case. In this case, referring to FIG. 4, the receive coil 8, 10 is de-tuned during the r.f. excitation pulse, by inductively coupling resistance from the pick-up coil 11, 13 into the receive coil 8, 10.

The receive coil 8, 10 together with tuning capacitor $C_{tune}$ form a resonant L-C circuit with a series resistance $r_1 = \omega . L_1 / Q_1$. For a well designed coil, $Q_1$ is maximised, $r_1$ is small and large currents are free to circulate. If the pick-up coil 11, 13 is also resonant and since it couples magnetically with the first, $$r = [\omega.L_1/Q_1] + [\omega^2.M^2/r_2]$$

where r is the series resistance of the receive coil when inductively coupled to resonant pick-up coil, M is the mutual inductance between the coils and $r_2$ is the resistance in the pick-up coil. The term $\omega^2.M^2/r_2$ is an additional resistance introduced in series with the receive coil by mutual coupling. Since $M^2 = k^2.L_1.L_2$ where k is the coefficient of coupling and $L_1$ and $L_2$ are the respective coil inductances, $$r = \omega.L_1/Q_1 + \omega.k^2.L_1.L_2/r_2$$

but $Q_2 = \omega.L_2/r_2$, $Q_1 = \omega.L_1/r_1$ hence $r/r_1 = 1 + k^2.Q_1.Q_2$ The term $r/r_1$ would be unity if there was no inductive coupling of a resonance circuit and considerably greater than unity when there is inductive coupling of a resonant circuit. $C_{match/de-tune}$ is chosen so that it resonates with the pick-up coil at the resonant frequency of the receive coil when PIN diode 18 is switched on. This is done during the r.f. excitation pulses ($B_1$ pulses) of the magnetic resonance imaging process. This causes increased resistance in the receive coil which is therefore de-tuned during the $B_1$ pulses.

During the relaxation process when the protons in the patient which have been re-orientated in the main magnet field $B_0$ during the $B_1$ pulse, return to their original state, emitting r.f. energy, the PIN diode is switched off so that the receive coil is again resonant.

Coil coupling performance is therefore optimised by maximising k and $Q_2$. The practical value of k is limited by the relative diameters of the receiver coil and the pick-up coil which is constrained to pass within one of the endoscope service channels. There will be an optimum alignment for the coils (corresponding to the angular position at which the former 9 is attached) for which k is maximised.

A further requirement is that the receiver coil and is switched off. This impedance is a function of both k and $L_2$. However, maximum $Q_2$ may not be achieved with the value of $L_2$ required to give $Z_{out}$=50 ohms. This problem may be overcome by the addition of a $\lambda/4$ impedance transformer 16 to transform the input impedance seen across the diode into 50 ohms.

The circuit of FIG. 4 applies to each of FIGS. 1 to 3.

However, if desired, in place of the active de-tuning of FIG. 4, known passive de-tuning may be employed, for example, by using anti-parallel diodes across the output of the receive coil 11, thereby avoiding the need for the PIN diode 18 and the need to switch it at the $B_1$ pulses. Another alternative would be to use the receive and pick-up coils for transmission as well as for reception. There would then be no need to de-tune the receive coil during the $B_1$ pulses.

While the endoscopes of FIG. 3 have been described as being suitable for use with a set of coils, the inductive coupling giving the advantage of the avoidance of the need for plugs and sockets for the receive coil, would also be applicable if the endoscope was provided with a single coil, and the advantage of repair or replacement would still apply.

We claim:

1. An apparatus comprising:
   an MR compatible endoscope having a distal end;
   a former selectively mountable to the distal end;
   a receive coil carried by the former;
   a pick-up coil located at the distal end and inductively coupled to the receive coil when the former is mounted to the distal end whereby a signal detected by the receive coil is passed to the pickup coil.

2. The apparatus of claim 1 further comprising capacitive means selectively connectable to the pick-up coil to form a resonant circuit at the resonant frequency of the receive coil so as to couple inductively resistance from the pick-up coil into the receive coil to de-tune the receive coil.

3. The apparatus of claim 2 further comprising a PIN diode for selectively connecting the capacitive means to the pick-up coil.

4. The apparatus of claim 2 further comprising a quarter wave transformer adapted to match the pick-up coil and the capacitive means to a desired impedance.

5. The apparatus of claim 1 wherein the endoscope comprises a service channel and the pick-up coil is located in a service channel.

6. The apparatus of claim 5 wherein the pick-up coil is selectively removable from the service channel.

7. The apparatus of claim 1 wherein the distal end comprises an outer portion, the former comprises an inner portion, and the inner portion of the former is adapted to fit over the outer portion of the distal end.

8. The apparatus of claim 1 wherein the receive coil comprises a pair of saddle coils.

9. The apparatus of claim 1 wherein the receive coil is recessed into the surface of the former.

10. An MR compatible endoscope provided with a plurality of interchangeable receive coils, each of the plurality of receive coils adapted to operate in a main magnetic field having an associated field strength, whereby the same endoscope may be used at a plurality of main magnetic field strengths by using an appropriate one of said receive coils with the endoscope.

11. The endoscope of claim 10 wherein each receive coil is carried by a former which is selectively removable from a distal end of the endoscope.

12. The endoscope of claim 11 further comprising a pick-up coil disposed at the distal end of the endoscope such that the receive coil and the pick-up coil are inductively coupled when the former is mounted to the distal end, whereby a radio frequency signal generated in response to a magnetic resonance excitation sequence and received by the receive coil is coupled to the pickup coil.

13. The endoscope of claim 12 further comprising capacitive means selectively connectable to the pick-up coil to form a resonant circuit at the resonant frequency of the receive coil so as to couple inductively resistance from the pick-up coil into the receive coil to de-tune the receive coil.

14. The endoscope of claim 13 further comprising a PIN diode for selectively coupling the capacitive means to the pick-up coil.

15. The endoscope of claim 14 further comprising a quarter wave transformer, the transformer matching the pick-up coil and the capacitive means to a desired impedance.

16. The endoscope of claim 11 wherein former may be slid over the distal end of the endoscope.

17. The endoscope of claim 10 wherein the pickup coil is selectively insertable in a service channel of the endoscope.

18. The endoscope of claim 11 wherein a pick-up coil is housed in a distal end of the endoscope, the pick-up coil being inductively coupled to the receive coil when the formeris mounted to the distal end of the endoscope.

19. The endoscope of claim 17 further comprising a coaxial cable connected to the pick-up coil.

20. An apparatus comprising:
   a endoscope having a proximal and a distal end;
   a former which is demountable with respect to the distal end of the endoscope;
   a receive coil for detecting magnetic resonance signals generated by a magnetic resonance imaging procedure;
   a pick-up coil located in the distal end of the endoscope and inductively coupled to the receive coil when the former is mounted to the distal end of the endoscope; and
   means for passing an electrical signal from the pick-up coil to the proximal end of the endoscope.

* * * * *